US010297123B2

(12) United States Patent
Levesque et al.

(10) Patent No.: US 10,297,123 B2
(45) Date of Patent: May 21, 2019

(54) WEARABLE ARTICLE HAVING AN ACTUATOR THAT PERFORMS NON-HAPTIC AND HAPTIC OPERATIONS

(71) Applicant: Immersion Corporation, San Jose, CA (US)

(72) Inventors: Vincent Levesque, Montreal (CA); Vahid Khoshkava, Laval (CA)

(73) Assignee: IMMERSION CORPORATION, San Jose, CA (US)

( * ) Notice: Subject to any disclaimer, the term of this patent is extended or adjusted under 35 U.S.C. 154(b) by 0 days.

(21) Appl. No.: 16/110,272

(22) Filed: Aug. 23, 2018

(65) Prior Publication Data

US 2018/0365941 A1   Dec. 20, 2018

Related U.S. Application Data

(63) Continuation of application No. 14/974,963, filed on Dec. 18, 2015, now Pat. No. 10,102,722.

(51) Int. Cl.
| | | |
|---|---|---|
| *G08B 6/00* | (2006.01) | |
| *A43B 11/00* | (2006.01) | |
| *A61B 5/00* | (2006.01) | |
| *A41D 1/00* | (2018.01) | |
| *G06F 3/01* | (2006.01) | |
| *G06F 1/16* | (2006.01) | |

(52) U.S. Cl.
CPC .............. *G08B 6/00* (2013.01); *A41D 1/002* (2013.01); *A43B 11/00* (2013.01); *A61B 5/6802* (2013.01); *G06F 1/163* (2013.01); *G06F 3/016* (2013.01); *A61B 5/6807* (2013.01)

(58) Field of Classification Search
None
See application file for complete search history.

(56) References Cited

U.S. PATENT DOCUMENTS

| 8,004,391 B2 | 8/2011 | Hernandez |
| 8,523,740 B2 | 9/2013 | Kruse et al. |
| 8,621,348 B2 | 12/2013 | Ramsey et al. |
| 8,659,571 B2 | 2/2014 | Birnbaum et al. |

(Continued)

FOREIGN PATENT DOCUMENTS

| WO | 2009134858 A1 | 11/2009 |
| WO | 2014022667 A1 | 2/2014 |

OTHER PUBLICATIONS

Ericson, "Sensing shape and motion with bistable switches that digitize material strain—caused by flexure," Retrieved from http://home.earthlink.net/-barkingpo/shapesensor.html, 8 pages, Feb. 1, 2018.

(Continued)

*Primary Examiner* — John F Mortell
(74) *Attorney, Agent, or Firm* — Miles & Stockbridge P.C.

(57) ABSTRACT

A haptic zipper is provided. The haptic zipper includes a first chain, a second chain opposing the first chain, a slider, an actuator coupled to the slider, and a controller coupled to the actuator. The slider is coupled to the first chain and the second chain to mesh or disengage opposing teeth of the first and second chains. The controller is configured to process an input signal including data related to a haptic effect, generate a haptic drive signal based on the data, and transmit the haptic drive signal to the actuator to render the haptic effect.

13 Claims, 7 Drawing Sheets

(56) References Cited

U.S. PATENT DOCUMENTS

| | | |
|---|---|---|
| 8,769,844 B2 | 7/2014 | Beers et al. |
| 8,896,524 B2 | 11/2014 | Birnbaum et al. |
| 8,976,112 B2 | 3/2015 | Birnbaum et al. |
| 9,019,087 B2 | 4/2015 | Ullrich et al. |
| 9,671,626 B2 | 6/2017 | Levesque et al. |
| 2009/0167677 A1 | 7/2009 | Kruse et al. |
| 2009/0305744 A1 | 12/2009 | Ullrich |
| 2010/0060466 A1* | 3/2010 | Austin .................... G08B 6/00 340/628 |
| 2010/0152545 A1 | 6/2010 | Ramsay et al. |
| 2011/0264491 A1 | 10/2011 | Birnbaum et al. |
| 2011/0310043 A1 | 12/2011 | Lacroix et al. |
| 2014/0313040 A1* | 10/2014 | Wright, Sr. ............ G08B 17/10 340/628 |
| 2014/0360047 A1 | 12/2014 | Beers et al. |
| 2015/0072789 A1 | 3/2015 | Heubel et al. |
| 2015/0145656 A1 | 5/2015 | Levesque et al. |
| 2016/0165965 A1* | 6/2016 | Ellis ....................... A41D 1/002 434/81 |
| 2016/0255944 A1* | 9/2016 | Baranski .............. A44C 5/0069 |
| 2017/0076564 A1* | 3/2017 | Cruz-Hernandez ...... G08B 6/00 |
| 2017/0086513 A1* | 3/2017 | Maxey ............... A41D 13/0051 |
| 2017/0146358 A1* | 5/2017 | Ward ..................... G06F 3/016 |

OTHER PUBLICATIONS

Vincent, (Oct. 22, 2015)."Watch Michael J. Fox demonstrate Nike's self-lacing sneakers on Kimmel," Retrieved rom https://www.theverge.com/2015/10/22/9591656/self-lacing-sneakers-kimmel, 4 pages.

Definition of shape memory materials, Retrieved from http://image.slidesharecdn.com, 2 pages, Oct. 4, 2015.

* cited by examiner

WEARABLE ARTICLE HAVING AN ACTUATOR THAT PERFORMS NON-HAPTIC AND HAPTIC OPERATIONS

CROSS-REFERENCE TO RELATED APPLICATIONS

This application is a continuation of U.S. patent application Ser. No. 14/974,963, filed on Dec. 18, 2015, the disclosure of which is incorporated herein by reference in its entirety.

TECHNICAL FIELD

This patent document relates to haptic effects, and more particularly to wearable articles that have an actuator that performs a non-haptic operation and a haptic operation.

BACKGROUND

Actuated clothing that automatically fastens to a person's body or that automatically adjust their fit are being developed. Examples include shoes that automatically lace themselves, zippers that automatically open and close, and belts that automatically tighten. Other examples of actuated clothing include clothing that automatically change their porosity based on conditions such as moisture, ambient temperature, body temperature, and other environmental or biometric factors.

Such actuated clothing has several existing and as yet unforeseen advantages such as minimizing the effort to dress of people who are lazy or in a hurry, enabling people with limited mobility to dress themselves and retain a level of independence and dignity, or automatically adjusting the enhance a person's comfort.

SUMMARY

Embodiments of the present invention provide a haptic zipper.

In one embodiment, a haptic zipper includes a first chain, a second chain opposing the first chain, a slider, an actuator coupled to the slider, and a controller coupled to the actuator. The slider is coupled to the first chain and the second chain to mesh or disengage opposing teeth of the first and second chains. The controller is configured to process an input signal including data related to a haptic effect, generate a haptic drive signal based on the data, and transmit the haptic drive signal to the actuator to render the haptic effect.

DETAILED DESCRIPTION

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," "including," "has," and "having" are interchangeable and not intended to be limiting. The term "such as" also is not intended to be limiting. For example, the term "including" shall mean "including, but not limited to."

In general terms, this patent document relates to articles wearable by a person in which the article has an actuator that performs a non-haptic operation and a haptic operation.

Figure 1:
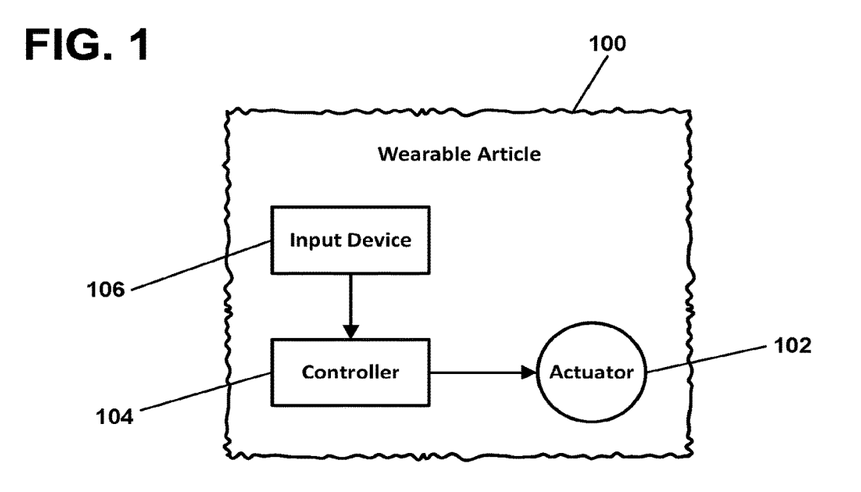
FIG. 1 is a block diagram illustrating an embodiment of a wearable article that is has an actuator that performs non-haptic and haptic operations.

Referring now to FIG. 1, a wearable article 100 has an actuator 102, a controller 104, and an input device 106. The wearable article 100 can be any type of thing worn by a person. Examples of wearable articles 100 include clothing; footwear; prosthetics such as artificial limbs; headwear such as hats and helmets; athletic equipment worn on the body; protective equipment such as ballistic vests, helmets, and other body armor; eyeglasses; accessories such as neckties and scarfs; belts and suspenders; jewelry such as bracelets, necklaces, and watches; and anything else that can be worn on the body.

The actuator 102 can be any controlled mechanism or other structure that initiates movement to perform an operation on the wearable article. Examples of operations performed by an actuator 102 include fastening the wearable article 100 to the person's body, adjusting the fit of the wearable article 100, or performing any other operation on the article 100. Various embodiments can include a single actuator or two or more actuators.

The input device 106 is any device that inputs a signal into the controller 104. An example of an input device 106 is a control device such as a switch. Another example of an input device 106 is a transducer that inputs a signal into the controller 104. Examples of transducers that can be used as an input device 106 include antennas and sensors. Various embodiments can include a single input device or can include two or more input devices. Additionally, various embodiments can include different types of input devices. For example, at least some possible embodiments include a switch and a transducer such as an antenna or a sensor.

The controller 104 is any type of circuit that controls operation of the actuator 102 based on receiving a signal or data from the input device 106. Data can be any type of parameters, instructions, flags, or other information that is processed by the processors, program modules, and other hardware disclosed herein.

In operation, the controller 104 and actuator 102 have a non-haptic operation. Examples of such operations include operating a fastener to close or secure a wearable article 100 on a person or adjusting the fit of a wearable article 100. The operation is performed by operating an input device 106 such as a switch. Non-haptic operation of an actuator 102 may cause tactile sensation to a person, but is not intended to convey a particular message such as a cue, notification, or other information.

The controller 104 and actuator 102 also have a haptic operation. In such an operation, an input device 106 is stimulated and inputs a signal to the controller 104. In response, the controller 104 operates the actuator 102 to provide haptic feedback to the person wearing the article 100. The haptic feedback typically embodies a message to the person wearing the article 100. The message can be a notification or can contain other types of more complex information. Haptic operation of the actuator 102 can be such that it is distinguishable from non-haptic operation. For example, an automated belt, as described in more detail herein, can be automatically tightened at a slower rate during non-haptic operation. The belt then can be tightened at a quicker rate or according to particular pattern of movement during haptic operation.

A haptic effect can be any type tactile sensation delivered to a person. The haptic effect embodies a message such as a cue, notification, or more complex information.

Figure 2:
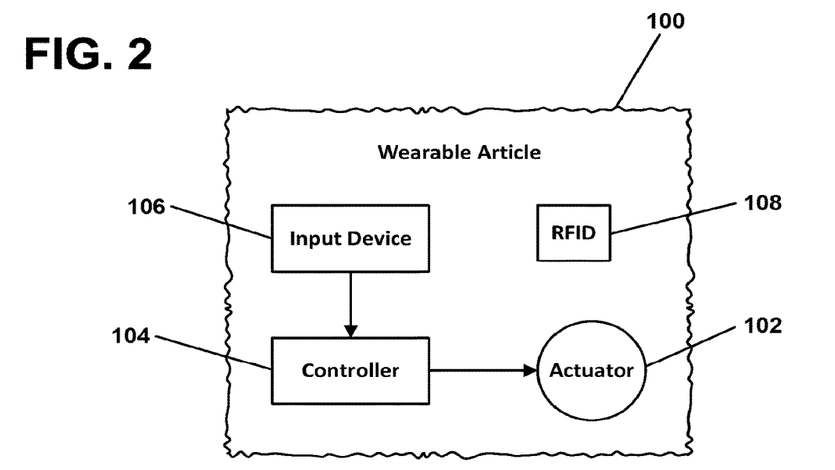
FIG. 2 is a block diagram illustrating an alternative embodiment of the wearable article illustrated in FIG. 1.

FIG. 2 illustrates an alternative embodiment of the wearable article 100 that is substantially similar to the wearable article illustrated in FIG. 1 and also includes the input device 106, controller 100, and actuator 102.

The wearable article 100 in this embodiment also includes an RFID tag 108 that stores identifying information. Examples of identifying information that can be stored on the RFID tag 108 include information identifying the person wearing the wearable article 100, the type of wearable article 100, the specific wearable article that includes the RFID tag, the type of actuator 102 included on the wearable article 100, or any other information.

In this embodiment, the wearable article 100 includes at least one input device 106 that is an antenna for receiving a signal that embodies data associated with a haptic message.

The embodiment illustrated in FIG. 2 has many applications, including use in an environment that has a network that provides communication between an RFID reader and a remote device. In operation, a person moves near the RFID reader that detects the RFID tag 108 and reads the identifying information, which in turn is sent to the remote device. In response to receiving the identifying information, the remote device determines whether to deliver data associated with a haptic effect to the wearable article 100. If the computing device determines to send data, a signal is generated and transmitted to the antenna. The antenna receives the signal, which is processed by the controller 104. The controller 104 then controls the actuator 102 to deliver the haptic message.

Other embodiments can be used in an environment that uses hardware, software, and systems other than RFID tags and readers to communicate between the controller 104 and a remote device or network. For example, the wearable article 100 could have a Bluetooth transceiver in data communication with the controller 104. The Bluetooth receiver could provide data communication or presence sensing with a Bluetooth beacon that is in communication with the remote device. In this example, the Bluetooth beacon could periodically broadcast haptic messages or other data that are received by the Bluetooth receiver and processed by the controller 104. In another example, a camera or other imaging device could be in data communication with the remote device and provide the remote device with images of a person's face or particular items of clothing. If remote device recognizes the person's face or item of clothing, it can then determine whether a haptic message or other data should be sent to the controller and send the haptic message or data to the controller 104, which would then processes it.

Figure 3:
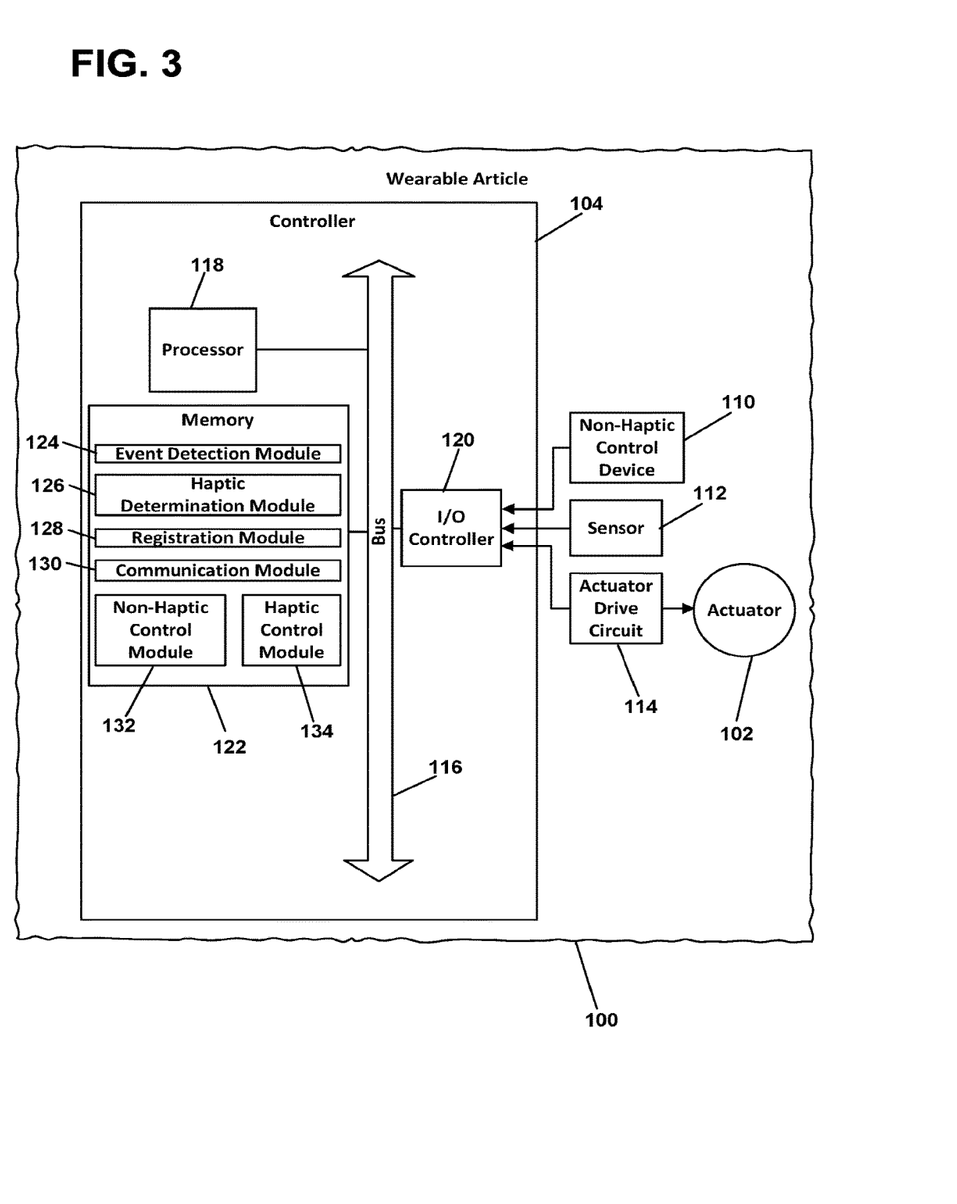
FIG. 3 is a block diagram illustrating the wearable article shown in FIG. 1 in more detail.

FIG. 3 illustrates a more detailed block diagram of a possible embodiment of the wearable article 100 illustrated in FIG. 1.

In this embodiment, the wearable article 100 includes the actuator 102 and the controller 104. Two input devices are in electrical communication with the controller and include a non-haptic control device 110 and a sensor 112. An actuator drive circuit 114 is in electrical communication with the controller 104 and the actuator 102.

The actuator 102 can be any device that produces a motion. Examples of actuators include mechanisms such as motors; linear actuators such as solenoids; magnetic or electromagnetic mechanisms; and smart materials such as shape memory alloys, piezoelectric materials, electroactive polymers, and materials containing smart fluids.

The non-haptic control device 110 is an input device that initiates performance of the non-haptic operation. An example of a non-haptic control device 110 is a switch that a person manually actuates. Another example includes switches that are automatically executed upon certain conditions. Yet another example of the non-haptic control device 110 includes an antenna that receives a signal that communicates an instruction or a sensor output associated with a detected condition. A switch can be any mechanism that makes, breaks, or changes a connection in a circuit.

The sensor 112 can be any instrument or other device that outputs a signal in response to receiving a stimulus. The sensor 112 can be hardwired to the controller 104 or can be connected to the controller 104 wirelessly. The sensor 112 can be used to detect or sense a variety of different conditions, events, and things such as non-haptic operation of the actuator 102 or wearable article 100, haptic operation of the actuator 102 or wearable article 100, the physical condition of the wearable article 100, environmental conditions, or the presence of other people or objects.

Examples of sensors 112 include acoustical or sound sensors such as microphones; vibration sensors; chemical and particle sensors such as breathalyzers, carbon monoxide and carbon dioxide sensors, and Geiger counters; electrical and magnetic sensors such as voltage detectors or hall-effect sensors; flow sensors; navigational sensors or instruments such as GPS receivers, altimeters, gyroscopes, or accelerometers; position, proximity, and movement-related sensors such as piezoelectric materials, rangefinders, odometers, speedometers, shock detectors; imaging and other optical sensors such as charge-coupled devices (CCD), CMOS sensors, infrared sensors, and photodetectors; pressure sensors such as barometers, piezometers, and tactile sensors; force sensors such as piezoelectric sensors and strain gauges; temperature and heat sensors such as thermometers, calorimeters, thermistors, thermocouples, and pyrometers; proximity and presence sensors such as motion detectors, triangulation sensors, radars, photo cells, sonars, and hall-effect sensors; biochips; biometric sensors such as blood pressure sensors, pulse/ox sensors, blood glucose sensors, and heart monitors. Additionally, the sensors 112 can be formed with smart materials, such as piezo-electric polymers, which in some embodiments function as both a sensor and an actuator. Additional sensors are disclosed in U.S. Pat. No. 8,659,571 issued on Feb. 25, 2014 and entitled Interactivity model for shared feedback on mobile devices, the entire disclosure of which is hereby incorporated by reference.

With the wearable article 100 including an antenna or sensor, the controller 104 can receive input or feedback about the operation or state of the wearable article 100 including non-haptic operation, haptic operation, and the state of the article 100 such as whether the article 100 has any worn areas, the state of fasteners on the article 100, or positioning of the article 100 on a person. The controller 104 can process the signal, information, or data input and then control the actuator 102 to deliver a haptic message related to the operation of state of the wearable article 100. The controller 104 also can receive input or feedback related to conditions, aspects, and things other than the operation or state of the wearable article 100 itself. For example, it can receive information about environmental conditions to which the wearable article 100 is exposed or might be exposed, information about the conduct or movement of the person wearing the wearable article 100, and any other information that can be sensed by sensor 112 or otherwise delivered to the controller 104.

The actuator drive circuit 114 is a circuit that receives a haptic signal from the controller 104. The haptic signal embodies haptic data, and the haptic data defines parameters the actuator control circuit 114 uses to generate a haptic drive signal. Examples of parameters that can be defined by the haptic data includes frequency, amplitude, phase, inversion, duration, waveform, attack time, rise time, fade time, and lag or lead time relative to an event. The haptic drive signal is applied to the actuator 102.

The controller 104 comprises a bus 116, processor 118, input/output (I/O) controller 120, and memory 122. The bus 116 includes conductors or transmission lines for providing a path to transfer data between the components in the controller 104 including the processor 118, memory 122, and I/O controller 120. The bus 116 typically comprises a control bus, address bus, and data bus. However, the bus 116 can be any bus or combination of busses, suitable to transfer data between components in the controller 104.

The I/O controller 120 is circuitry that monitors operation of the controller 104 and peripheral or external devices such as the non-haptic control device 110, the sensor 112, and the actuator drive circuit 114. The I/O controller 120 also manages data flow between the controller 104 and the peripheral devices and frees the processor 118 from details associated with monitoring and controlling the peripheral devices. Examples of other peripheral or external devices with which the I/O controller 120 can interface includes external storage devices; monitors; input devices such as keyboards, pointing devices; external computing devices; antennas; other articles worn by a person; and any other remote devices.

The processor 118 can be any circuit configured to process information and can include any suitable analog or digital circuit. The processor 118 also can include a programmable circuit that executes instructions. Examples of programmable circuits include microprocessors, microcontrollers, application specific integrated circuits (ASIC), programmable gate arrays (PLA), field programmable gate arrays (FPGA), or any other processor or hardware suitable for executing instructions. In various embodiments, the processor 118 can be a single unit or a combination of two or more units. If the processor 118 includes two or more units, the units can be physically located in a single controller or in separate devices.

The memory 122 can include volatile memory such as random access memory (RAM), read only memory (ROM), electrically erasable programmable read only memory (EPROM), flash memory, magnetic memory, optical memory, or any other suitable memory technology. The memory 122 also can include a combination of volatile and nonvolatile memory.

The memory 122 can store a number of program modules for execution by the processor 118, including an event detection module 124, a haptic determination module 126, a registration module 128, a communication module 130, a non-haptic control module 132, and a haptic control module 134. Each module is a collection of data, routines, objects, calls, and other instructions that perform one or more particular task. Although certain modules are disclosed herein, the various instructions and tasks described herein can be performed by a single module, different combinations of modules, modules other than those disclosed herein, or modules executed by remote devices that are in communication with the controller 104.

The event detection module 124 is programmed to receive data from the sensor 112, the antenna, or a remote device. Upon receiving the data, the event detection module 124 determines whether there is an event, condition, or operating state associated with a haptic effect.

Upon identification of an event associated with a haptic effect, the haptic determination module 126 analyzes the data received from the sensor 112, antenna, or remote device to determine a haptic effect to deliver through the actuator 102. An example technique the haptic determination module 126 can use to determine a haptic effect includes rules programmed to make decisions to select a haptic effect. Another example includes lookup tables or databases that relate haptic effects to data received from the sensor or antenna.

The haptic control module 134 generates a haptic signal upon the haptic determination module 126 identifying a haptic effect to deliver to the actuator 102. The haptic control module 134 receives haptic data and generates a haptic signal. The haptic control module 134 sends the haptic signal to the actuator drive circuit 114, which then generates the haptic drive signal. The haptic drive signal embodies the message to be conveyed to the person wearing the article 100.

Upon actuation of the non-haptic control device 110, the I/O controller 120 inputs non-haptic operational data to the controller 104. The non-haptic control module 132 receives the non-haptic operational data and generates a non-haptic operation signal, which is input to the actuator drive circuit 114. The actuator drive circuit 114 then generates a non-haptic drive signal and applies the non-haptic drive signal to the actuator 102. Also in various embodiments, the non-haptic control device and I/O controller 120 can input binary information into the controller 104 such as a flag indicating a simple on or off instruction. Alternatively, the non-haptic control device 110 and I/O controller 120 can input more complex information indicating more complex instructions for the non-haptic control module 132 to process and to provide more complex control of the actuator 102.

The registration module 128 receives and processes registration data such as device information, context information, or other data used for system functions. The device information may include identifying data such as an address or other data that can identify the wearable article 100, the type of wearable article 100, the type of hardware included in the wearable article 100, the person who is wearing the article 100, or the person to whom the article 100 belongs. The identifying information also can identify capability (e.g., whether the device is capable of providing haptic feedback, storing digital content, receiving user inputs, etc.) of the hardware included on the wearable article 100. Examples of addresses include media access control (MAC) addresses, uniform resource locators (URL), or other network addresses. The address data also can include port information identifying where communication channels may be established for transferring digital content, and/or other device information. In alternative embodiments, the registration data can be stored on the RFID tag 108.

By registering identifying data about the wearable article 100, and as discussed in more detail herein, remote devices may be made aware of the wearable article 100 so they can transfer data such as haptic data instructions to and from the wearable article 100.

Registration of wearable articles and communication of data to and from them is discussed in more detail in U.S. application Ser. No. 14/106,275, which was filed on Dec. 13, 2013 and is entitled METHOD AND APPARATUS OF BODY-MEDIATED DIGITAL CONTENT TRANSFER AND HAPTIC FEEDBACK, the entire disclosure of which is hereby incorporated by reference.

The communication module 130 facilitates communication between the controller 104 and remote devices. Examples of remote devices include computing devices, sensors, other wearable articles, exercise equipment, and smart appliances. Examples of computing devices include servers, desktop computers, laptop computers, tablets, smartphones, home automation computers and controllers, and any other device that is programmable. The communication can take any form suitable for data communication including communication over wireless or wired communication signal or data paths. In various embodiments, the communication module may configure the controller 104 as a centralized controller of wearable articles or other remote devices, as a peer that communicates with other wearable articles or other remote devices, or as a hybrid centralized controller and peer such that the controller can operate as a centralized controller in some circumstances and as a peer in other circumstances.

Alternative embodiments of the program modules are possible. For example, some alternative embodiments might have more or fewer program modules than the event detection module 124, haptic determination module 126, registration module 128, communication module 130, non-haptic control module 132, and haptic control module 134. For example, the controller 104 can be configured to deliver only a single haptic effect. Such embodiments might not have a haptic determination module 126, and the event detection module 124 or some other module would cause the haptic control module 134 to send the haptic data to the haptic control module 134. In other alternative embodiments, there is no event detection module 124 and the haptic control module 134 sends a haptic signal to the actuator control circuit 114 upon the controller 104 receiving an input from the sensor 112.

In some possible embodiments, one or more of the program modules are in remote devices such as remote computing devices or other wearable articles. For example, the event determination module 124 can be located in a remote computing device, which also stores a library of haptic effects and rules that define when to deliver a haptic effect. In such an embodiment, the controller 104 communicates data to the remote device when the event detection module 124 determines that a haptic effect should be delivered through the actuator 102. The data might be as simple as a flag indicating that the controller 104 received an input from the sensor 112, or more complex such as identifying the type of condition indicated by the sensor 112 or identifying the type of sensor 112 from which an input signal was received. The haptic determination module 126 on the remote device will process the data and instructions, retrieve matching haptic data from memory 122, and then transmit the haptic data to the controller 104 for processing and generating a haptic effect through the actuator 102. In yet other possible embodiments, the event detection module 124 is also located in a remote device, in which case the controller 104 communicates data to the remote device when it receives input from the sensor 112.

Figure 4:
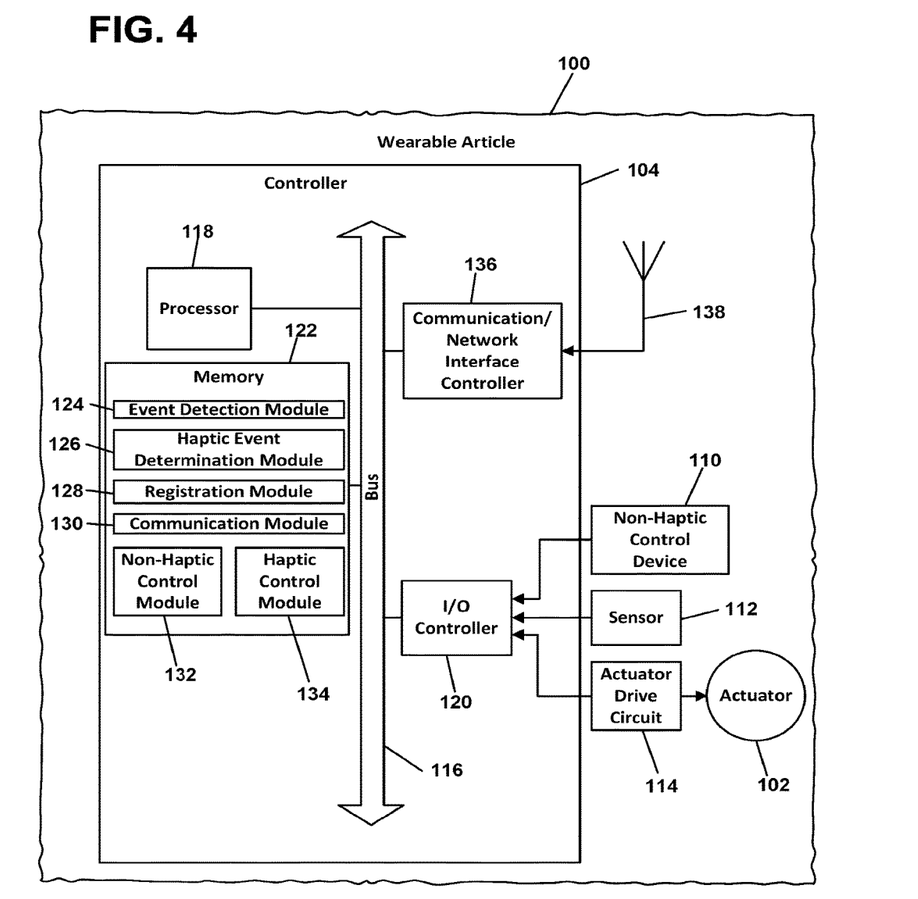
FIG. 4 is a block diagram illustrating the wearable article shown in FIGS. 1 and 3 having an additional input device.

The wearable article 100 illustrated in FIG. 4 is substantially similar to the wearable article illustrated in FIG. 3 and includes the controller 104, non-haptic control device 110, sensor 112, actuator drive circuit 114, and actuator 102. Additionally, the controller 104 includes a network interface controller (NIC) 106. An antenna 138 is in electrical communication with the NIC 136 and provides wireless communication between the controller 104 and remote devices. The communication module 130 is programmed to control communication through the antenna 138 including processing data embodied in signals received through the antenna 138 and preparing data to be transmitted to remote devices through the antenna 138. Communication can be according to any wireless transmission techniques including standards such as Bluetooth, cellular standards (e.g., CDMA, GPRS, GSM, 2.5G, 3G, 3.5G, 4G), WiGig, IEEE 802.11a/b/g/n/ac, IEEE 802.16 (e.g., WiMax).

The NIC 136 also can provide wired communication between the controller 104 and remote devices through wired connections using any suitable port and connector for transmitting data and according to any suitable standards such as RS 232, USB, FireWire, Ethernet, MIDI, eSATA, or thunderbolt.

Figure 5:
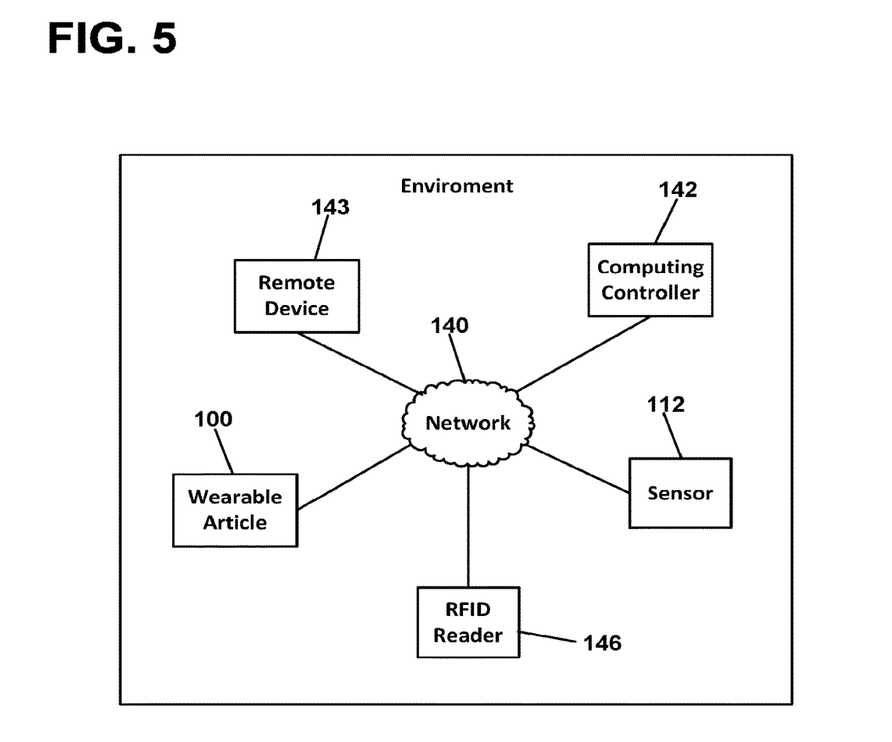
FIG. 5 is a block diagram illustrating a networked environment in which the wearable articles illustrated in FIGS. 1-4 can operate.

Referring now to FIG. 5 and discussed elsewhere in this disclosure, the wearable article 100 can operate within and communicate with a network 140 and remote devices. Examples of remote devices include computing devices 142, sensors 144, RFID readers 146, and other connected devices such as other wearable articles, exercise equipment, smart appliances, and other devices. In other embodiments, the network 140 provides data communication with different combinations of remote devices or remote devices other than those disclosed herein.

The network 140 operates in an environment 141 in which the wearable article 100 would be worn such as in a building, an automobile or other vehicles, or a defined area in the outdoors. Additionally, in various embodiments, the network 140 is a public network, private network, local area network, wide area network such as the Internet, or some combination thereof.

In various embodiments, the computing device 142 communicates with the controller 104 on the wearable article 100. In such embodiments, the computing device 142 executes program modules to process data and communicates data to the controller 104. For example, the computing device 142 receives input from a sensor 112, which could be in the wearable article 100 or remote from the wearable article 100. The computing device 142 then communicates the sensor data to the controller 104 in the wearable article 100. In another example, the computing device 142 receives data from one wearable device and relays that data to the controller in another wearable device to coordinate the delivery of haptic effects between different wearable articles. In another example, the computing device 142 receives data from other remote device 143 such as a smart appliance or exercise equipment and relays that data to the controller in the wearable article. In yet another possible embodiment, the controller 104 in the wearable article 100 communicates data such as sensor readings to the computing device 142, which then determines whether to deliver a haptic effect or what haptic effect to deliver. The computing device 142 then returns appropriate data to the controller 104.

In yet another possible example, the RFID reader 146 or some other sensor detects the presence of the RFID tag 108 and the presence of a wearable article 100 and communicates that presence to the computing device 142. The RFID reader 146 retrieves identifying data from the RFID tag 108 and communicates the retrieved identifying data to the computing device 142, which then processes the data and determines whether to communicate data to the controller 104 in the wearable article 100. The computing device 142 might execute a haptic determination module 126. If the haptic determination module 126 determines to deliver a haptic effect, the computing device 142 might communicate data associated with a haptic effect to the controller 104 of the wearable article 100, which then delivers the haptic effect through the actuator 102. The determination of whether to deliver a haptic effect can be based on a variety of factors including the identifying data retrieved from the RFID tag 108, or a combination of identifying data retrieved from the RFID tag 108 and additional data such as input from a sensor 112 or data such as weather reports received from a third party source.

Additionally, in various embodiments, the haptic data defining the haptic effect and defining the parameters for the haptic drive signal can be determined by the computing device 142. If there is only one available haptic effect, the computing device 142 retrieves the haptic data upon determining an event associated with a haptic effect has occurred. The computing device 142 communicates that haptic data to the controller 104 in the wearable article 100 for processing. Alternatively, the computing device 142 executes a haptic determination module 126 to identify the haptic effect that corresponds to the identifying data.

Figure 6:
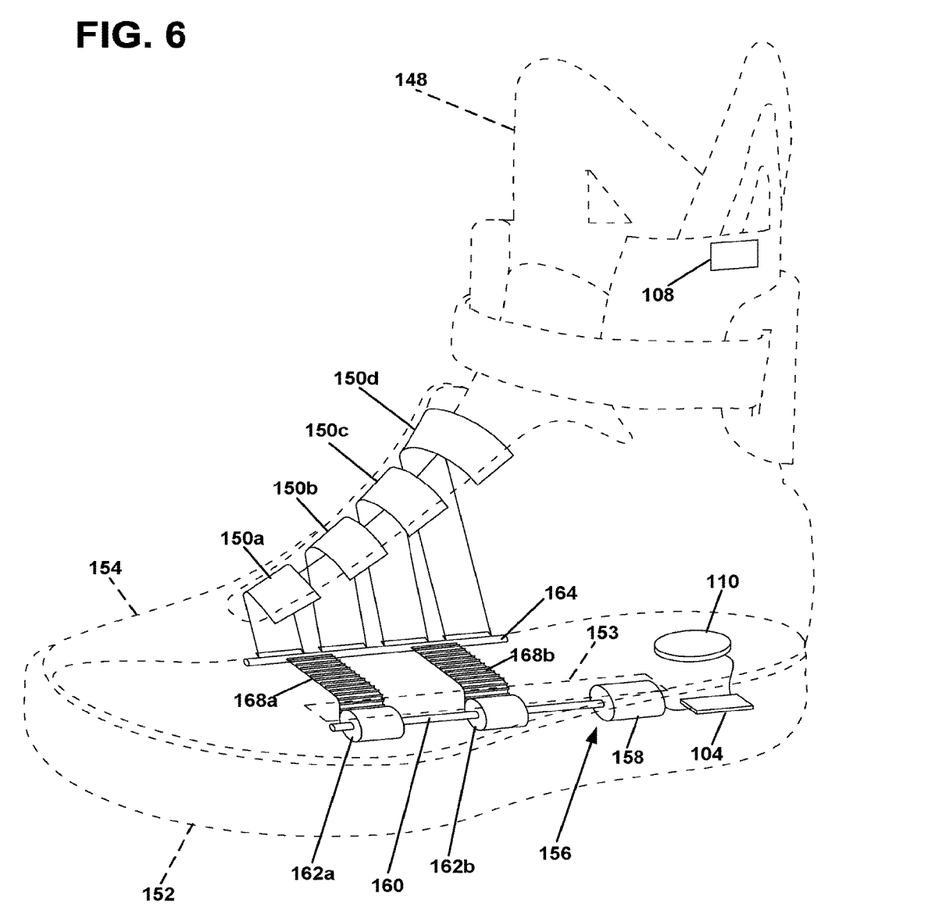
FIG. 6 is a partial isometric view illustrating a shoe having an automated lacing system having an actuator that performs non-haptic and haptic operations.

In an example application, when a person wearing actuated foot wear similar to shoe illustrated in FIG. 6, and discussed in more detail herein, begins to walk from the indoors to the outdoors, they will pass near and RFID reader 146 positioned near the door. The RFID reader 146 will detect the presence of the actuated shoe and communicate this presence to the computing device 142. If the computing device 142 receives information that there is inclement weather such as rain, it will transmit data associated with a haptic effect and associated with a message indicating the person should change to boots, grab an umbrella, or put on a raincoat.

In another example a person who is trying to lose weight is wearing an actuated article 100 such an automated belt. The person approaches a refrigerator equipped with an RFID reader 146 or other proximity detector, which detects the presence of the actuated belt and communicates this presence to the computing device 142. The computing device 142 then transmits data to the controller 104, which is on the belt. The transmitted data is associated with a haptic effect and message advising the person to be careful of the food they select.

In yet another example, a person wearing an actuated article 100 such as a necktie is in a meeting or in quiet area and receives a call on their smartphone. The phone is aware of the actuated article 100 and determines that the call is an emergency. The phone then sends a signal to the actuated article 100 associated with a haptic effect and a message that the call is important and needs to be answered as soon as possible. In this example, the necktie comprises smart material, which causes the necktie to tighten either temporarily or until the emergency call is connected.

In another example, the haptic track for a video or movie can be played back through wearable articles 100. In this example, operation of the actuator 102 can be coordinated with events or emotions presented in a movie. Operating the actuator 102 to suddenly or repeatedly tighten and loosen can be coordinated with an explosion in a movie, or the actuator could tighten the wearable article in particularly tense scenes. Operation of the actuator 102 in a wearable article can be similarly coordinated with events and emotions in video games such as when a character is shot in a combat oriented game, there is a crash in a racing game, or a collision in a sports game.

The actuator 102 also can be operated to provide feedback when a user is interacting with a user interface. For example, an actuator in the cuff of a shirt, a belt, zipper, or other article of clothing can be vibrated or moved to provide haptic feedback when using buttons, pointing devices such as a mouse or pen, or other controls and objects when interfacing with a user interface for a computer, smartphone, gaming console, including user interfaces that are based in physical environments or in virtual reality.

Other examples and applications of haptic enabled clothing are possible as well, including the examples provided in U.S. application Ser. No. 14/106,275, which was filed on Dec. 13, 2013 and is entitled METHOD AND APPARATUS OF BODY-MEDIATED DIGITAL CONTENT TRANSFER AND HAPTIC FEEDBACK, the entire disclosure of which was incorporated by reference. In one such example disclosed in U.S. application Ser. No. 14/106,275, the actuators 102 can be operated to deliver a sensation of flow. In this example, operation of different actuators 102 in a single wearable article 100 or in multiple wearable articles can be coordinated to increase the area that a person feels the flow sensation.

Various embodiments of the wearable device 100 also can operate independently of a remote device. For example, a shoe, belt, necktie, safety equipment, or medical equipment could include a pressure sensor that inputs a signal to the controller 104 for processing. If the controller determines that the wearable article is too tight or loose, it could control the actuator 102 to deliver a haptic message indicating the wearable article is too tight or loose. In a shoe for example, if the foot of a runner or other person begins to swell making the shoe too tight, the actuator 102 might deliver a haptic message to prompt the person to loosen the shoe. In another example, a helmet might have a series of sensors to detect, the positioning on a person head or whether chin strap is secured. The controller 104 can receive input from the sensors, determine whether there is a misfit, and then control the actuator 102 to deliver a haptic message if there is a misfit. Wearable articles such as helmets also could include sensors to detect a structural failure, such as a crack, in the helmet material. If the sensors input a signal indicative of a failure in the helmet, the controller 104 could then control the actuator 102 to deliver a haptic message indicating the failure. FIG. 6 illustrates one possible embodiment of a wearable article. In this embodiment, the wearable article is a shoe 148 having automated laces $150_a$-$150_d$. The shoe 148 includes a sole 152, an upper portion 154 connected to the sole 152, laces or straps 150$_a$-150$_d$, and an automatic lacing system 156. The sole 153 defines a cavity 153. The upper portion 154 defines a gap to allow the upper portion 154 to expand and make room for inserting the wearer's foot.

The automatic lacing system 156 includes motor 158 having a drive shaft 160 and first and second pulleys 162$_a$ and 162$_b$ mounted on the drive shaft 160. The motor 158, drive shaft 160, and pulleys 162$_a$ and 162$_b$ are positioned in the cavity. The automatic lacing system 156 also includes a yoke 164 positioned in a slot (not shown), which is defined in the sole 152 and extends from the cavity 153 to a position proximal to the upper portion 154 of the shoe 152. First and second belts 168$_a$ and 168$_b$ have one end connected to the first and second pulleys 162a and 162$_b$, respectively. The belts 168$_a$ and 168$_b$ extend through the slot and have an opposite end connected to a yoke 164, which also is positioned in the slot.

The straps 150$_a$-150$_b$ have first ends connected to the upper portion 154 proximal to one side edge of the gap. The straps then extend over the gap, along an opposite side of the upper portion 154 and into the slot 166. The opposite ends of the straps 150$_a$-150$_d$ are connected to the yoke 164. In operation, the motor 158 rotates the pulleys 162$_a$ and 162$_b$ in one direction to pull or take up the belts 168$_a$ and 168$_b$, which in turn pulls the yoke 164 closer to the pulleys 162$_a$ and 162$_b$. The yoke 164 pulls the straps 150$_a$-150$_d$ and tightens or fastens the shoe 148 to the wearer's foot. To remove the shoe 148, the motor 158 turns the drive shaft 160 and pulleys 162$_a$ and 162$_b$ in the opposite direction, which releases or loosens the straps 150$_a$-150$_d$.

The controller 104 is positioned in the sole 152 and is in electrical communication with the motor 158 and a non-haptic control device 110 positioned on the surface of the sole 152. In this embodiment, the non-haptic control device 110 is a pressure sensitive switch that is actuated when the wearer inserts their foot and applies pressure to the switch, which causes the controller 104 to drive the motor 158 until the straps 150$_a$-150$_d$ are securely tightened. The pressure sensitive switch is also actuated when the wearer lifts their heel enough so that the force applied to the pressure sensitive switch is reduced a predetermined amount, which causes the controller 104 to drive the motor 158 until the straps 150$_a$-150$_d$ are loosened a predetermined amount. The self-lacing shoe 148 disclosed herein is substantially similar to Nike Air Mag shoes developed by Nike, Inc. having its principle place of business in Beaverton, Oreg., and also is substantially similar to the shoe disclosed in U.S. Pat. No. 8,769,844, issued on Jul. 8, 2014 and entitled AUTOMATIC LACING SYSTEM, the entire disclosure of which is hereby incorporated by reference.

Additionally, a sensor 112 is mounted in the shoe 148 and also is in electrical communication with the controller 104. As explained in more detail herein, the sensor 112 inputs a signal into the controller 104 upon sensing a predetermined condition. Upon receiving an input signal from the sensor 112 and depending on the embodiment, the controller 104 determines whether to deliver a haptic effect to the person wearing the shoe 148 and what haptic effect to deliver. Upon making this determination, the controller 104 generates a haptic signal and communicates the haptic signal to the actuator drive circuit (not shown in FIG. 6). The actuator drive circuit generates the haptic drive signal and applies it to the motor 158 to move the straps 150$_a$-150$_d$ in a predetermined pattern corresponding to the determined haptic effect and conveying the predetermined message.

The predetermined pattern can be any pattern that can communicate a message to the person wearing the shoe 148. For example, the controller 104 might repeatedly loosen and tighten the straps 150$_a$-150$_d$ a predetermined number of times or in a pattern, according to predetermined intervals or according to varying intervals. Another haptic effect might be tightening and loosening the straps 150$_a$-150$_d$ to have a longitudinal tension along its length that is different than the tension normally applied to the straps 150$_a$-150$_d$ when the shoe 148 is initially put on the person's foot. In yet another example, the tension of the straps 150$_a$-150$_d$ is changed or varied to provide a sequence of different tensions.

In alternative embodiments, the controller 104 can include an antenna 138 in addition to a sensor 112 so that the controller 104 can communicate with remote devices. In other embodiments, the controller 104 in the shoe 158 contains an antenna 138 and no sensor. The shoe 158 can also include an RFID tag 108.

Another alternative embodiment of a shoe that comprises smart material having an origami-type configuration that folds or transitions between a first shape that is flat or that has an enlarged opening to receive a foot, and a second shape that is molded around a person's foot. When a person steps into the shoe, a sensor detect the person's foot and inputs a signal to the controller. The controller then controls the smart material to bend from the first shape to the second shape molded around the person's foot. In this embodiment, the smart material also can vibrate when an external force such as an electric current or electric field is applied to it. In some embodiment, the smart material functions as the haptic actuator and the fastener, In other embodiment, the smart material functions as a sensor that outputs a signal when it detects the force of a foot and thus functions as the haptic actuator, fastener, and sensor.

Figure 7:
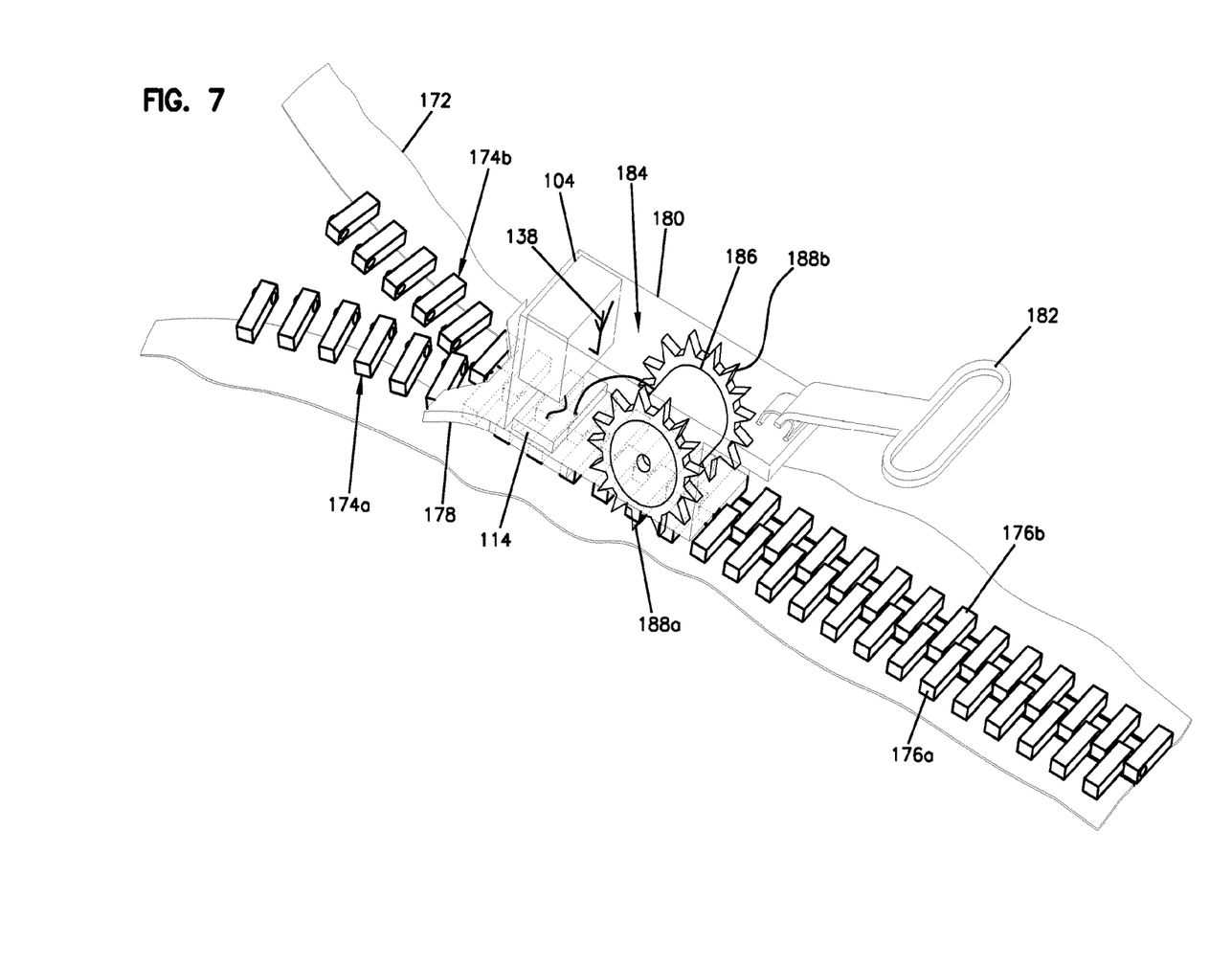
FIG. 7 is a partial isometric view illustrating an automated zipper which can be used in wearable articles having an actuator that performs non-haptic and haptic operations.

FIG. 7 illustrates an automated zipper 172 that can be included in wearable articles 100. The zipper 172 includes opposing chains 174$_a$ and 174$_b$, and each chain has teeth 176$_a$ and 176$_b$, respectively, positioned such that the teeth of one chain are offset relative to, and selectively mesh with, the teeth of the opposing chain. A slider 178 defines a Y-shaped channel that engages the opposing chains 174$_a$ and 174$_b$ and forces the opposing teeth 176$_a$ and 176$_b$ to mesh or disengage as the slider 178 is moved up and down the chains, respectively. A housing 180 is operably connected to the slider 178 and houses an automatic zipping system 184. A pull tab 182 is operably connected to the housing 180 and can be used to manually move the slider 178 along the length of the zipper 172. The slider 178 has a maximum length of travel between one position in which the zipper 172 is fully closed and an opposite position in which the zipper 172 is fully open.

The automatic zipping system 184 comprises a motor 186, two gears 188$_a$ and 188$_b$, a controller 104, a non-haptic input device 110 such as a switch, and an antenna 118. The two gears 188$_a$ and 188$_b$ are mounted on a drive shaft of the motor 186. One gear 188$_a$ has teeth that engage the gaps between the teeth 176$_a$ in one chain 174$_a$. The other gear 188$_b$ has teeth that engage the gaps between the teeth 176$_b$ in the opposing chain 174$_b$. In operation, the motor 186 rotates the gears in one direction to move the slider 178 up the chain 174$_a$ and 174$_b$ to close the zipper 172 and in the opposite direction to move the slider 178 down the chain to open the zipper 172.

As explained in more detail herein, the antenna 118 receives from a remote device a signal that embodies data related to a haptic effect. The controller 104 processes the received data and controls the motor 186 to move the slider 178 in a predetermined pattern to deliver a haptic effect. The haptic effect can be movement of the slider 178 a distance or range-of-motion less than the maximum length of travel for the slider. Other haptic effects can be delivered by repeatedly moving the slider 178 along the zipper 100 in an up and down pattern or in a particular sequence; intermittently moving the slider 178 in intervals, which can vary in length; moving the slider 178 in different velocity or acceleration patterns; or any other pattern or movement. Additionally, moving the slider 178 without receiving instructions from the person wearing the article can be a haptic effect.

When the user is manually pulling the slider 178, another possible haptic feedback can be urging the motor 186 and gears $188_a$ and $188_b$ to move the slider 178 in the direction opposite from the manual movement to provide force feedback. This force feedback can be delivered in a variety of patterns and magnitudes to deliver virtual detents along the length of the zipper or some other haptic effect, and to deliver different haptic messages. For example, the force feedback can be delivered intermittently to create a sequence of virtual detents as the slider 178 is moving along the length of the zipper to indicate that it is not recommended to loosen or open the zipper.

The virtual detents also can be used to provide a sense of the distance the fastener has traveled. For example, the actuator can periodically apply virtual detents every quarter inch or every centimeter. The virtual detents also can be applied when the fastener or actuator is being automatically operated. For example, an extra pulse can be periodically applied to the actuator as it is operating to cause it to jerk or temporarily change its the speed of operation.

In another example, the motor 186 can operate to provide force feedback or some other automated movement when the slider 178 hits or comes close to a stop, thereby signaling the user that the end of its range of motion. In this example, the slider or zipper would have a mechanism to determine relative position of the slider such as a force sensor, proximity sensor, encoder, or stepper motor. The slider 178 also can provide haptic feedback if the slider disengages with the one of the chains 174 of the zipper indicating the zipper and hence wearable article is fully open.

Alternative embodiments can include a sensor included in the automated zipping system 184 and in electrical communication with the controller 104. A sensor 112 can be used in addition to, or in place of, the antenna 138. Additionally, although a zipper 172 is illustrated, the embodiments disclosed herein can be applied to other types of fasteners such as other slide fasteners, buckles such as belt buckles, snaps, clips, clasps, buttons, smart materials, buttons, eye and hooks, hook and loop fasteners, laces, straps, or elastic bands.

Figure 8A:
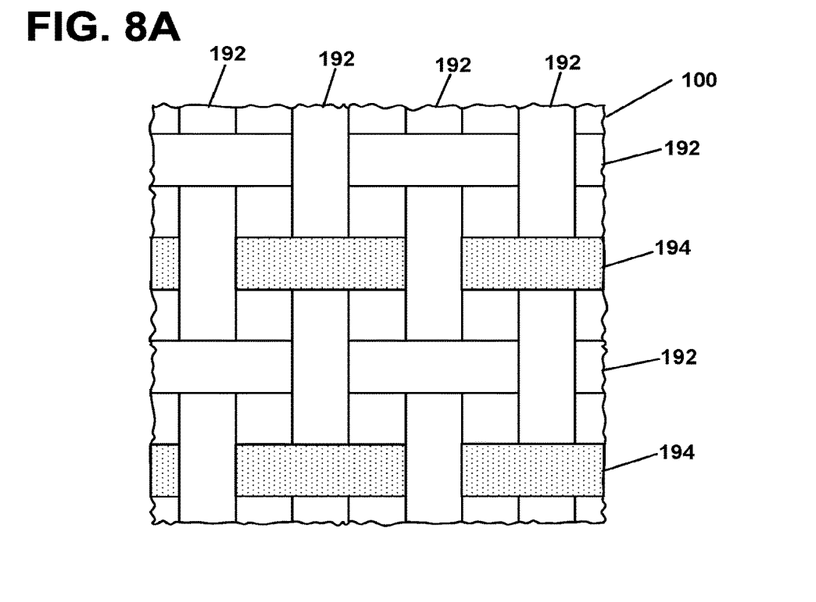
FIGS. 8A and 8B are partial isometric views of a wearable article having smart material that performs non-haptic and haptic operations.

FIG. 8A is a sectional view of some possible embodiments in which the actuator 102 comprises smart material. In this embodiment, the wearable article 100 is formed with a fabric woven with strands of a material 192 such as filaments, fibers, or yarns. The strands woven into the fabric includes one or more strands formed from a smart material 194. In the illustrated embodiments, the strands formed with smart materials 194 are oriented in one direction of the weave and are generally parallel to each other.

Figure 8B:
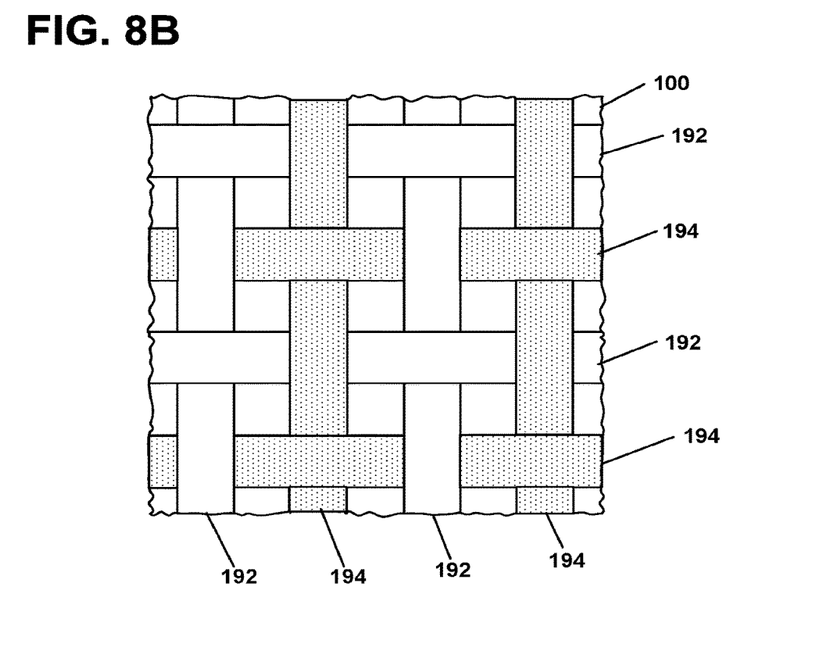

The number of strands formed with a smart material 194 will vary depending on the smart material, the non-haptic function of the smart material, and the ability of the smart material to deliver a sensation that is strong enough to be felt by the person wearing the article 100. Examples of non-haptic functions for the smart material includes adjusting the fit of the article, securing the article to the person wearing it, adjusting the porosity of the fabric based on conditions such as moisture, ambient temperature, body temperature, and other environmental or biometric factors. The controller and other components of the wearable article are not illustrated, but are similar to those discussed herein. FIG. 8B illustrates a weave that include strands formed with smart material 194, except that the weave includes at least one strand 194 woven in one direction and at least one strand 194 woven in a different, typically orthogonal direction. Various embodiments can include weaves that are different than the weaves illustrated in FIGS. 8A and 8B.

In alternative embodiments, the wearable article 100 is formed with strands that are knitted or braided, or a material other than strands such as polymers, leather, or metal. Additionally, the smart material in various embodiments is combined with the wearable article with a technique other than weaving, knitting, or braiding. For example, the smart material can be applied to a surface of the wearable article and held in place with an adhesive, stitches of thread, or a fastener. In another example, the smart material is embodied inside the material using techniques such molding the smart material into the wearable article.

In addition to the origami-type shoe and the embodiments disclosed herein, the smart material can function as a sensor, haptic actuator, and fastener in different types of wearable articles. For example, a shirt can have cuffs formed with a smart material that have a first expanded state and a second contracted state. When a person inserts their hand through the cuff, it transitions from the first state to the second state. The smart material replaces the cuff button, actuator, and haptic actuator.

An elastic or example waist of pants is another example, the waist is formed with a smart material that has a first elastic state and a second inelastic state. A person puts on the pants and the state of the smart material in the waste changes form the first state to the second state. The smart material functions as a belt, including the belt disclosed herein in more detail.

The smart material can be any material that changes a physical property in response to an external stimulus thereby modifying the wearable article 100 and causing a sensation that can be felt by a person wearing the article 100. The external stimulus can be applied to the smart material by the controller. Examples of stimuli that can control the smart material include potential differences, electrical currents, magnetic fields, or any other stimulus that can be generated, triggered, or controlled by the controller or a remote device communicating with the controller. In various embodiments, changing a physical property of the smart material will cause it to move relative to other strands or portions of the wearable article, vibrate, or change shape. In various embodiments, the smart material can have different types of movement such as linear movement, changes in the diameter or other dimensions of the smart material, and changes to the shape of the smart material. Examples of changes to the shape of a smart material can include bending, curving, transitioning between a spiral or helical shape and a straight configuration. Additionally, at least some embodiments, changes to the smart material are reversible and it can transition between two or more shapes or states.

Examples of smart material include shape memory alloys (such as temperature and magnetic shape-memory alloys), electroactive polymers having an electronic mechanism (such as electrostrictive, electrostatic, piezoelectric, and ferroelectric polymers), piezoelectric materials including piezo-polymers, conductive polymers, cellulose and other biopolymers, ionic polymer metal composites (IPMC), electrorheostatic materials, magnetorheostatic materials, magnetostrictive materials, pH-sensitive polymers, Peltier cells, ferrofluidic materials, and other fluidic materials. Additionally the smart material can be formed with or otherwise include nanoparticles or nanotubes. Examples of smart polymers include polyvinylidene fluoride (PVDF), polylactic acid (PLA), homo-polymers, co-polymers, and ter-polymers. The smart materials also can include polymer-metal composites and other combinations of different materials. Other examples include smart materials that move or change shape in response to forces such as temperature, electric currents, electric fields, Coulomb forces, mobility or diffusion of ions.

Additionally, the smart material can have a variety of states and structures such as fluids, solids, gases, gels, solids, elongated fibers, or panels, other shapes, and combinations thereof. Pneumatic structures such as gas bladders also can be used.

Additionally, the strands of smart material 194 can have a profile other than the traditional circular shape. The non-circular profile can help the strands of smart material 194 to move relative to other strands in the material, which can enable the wearable article 100 to contract or expand thereby tightening or loosening the wearable article, respectively. The non-circular shape also can be used to adjust the tightness of the weave, knit, or braid, or to adjust the porosity of the wearable article to enable it to vent, making it warmer or cooler. Changing the porosity also can make the wearable article more or less water repellent. Examples of alternative profile shapes include oval, square, or triangular. Different material can be added to the strand to form microscopic wings or propeller blades that also can help the strand of smart material move relative to the other strands in the article. In other possible embodiments, the smart material is formed into a structure other than a strand. A patch is an example of such an alternative structure for the smart material. Possible embodiments also can include fibers made of material that can cause the diameter of the fiber to change, which also can be used to adjust the tightness of the weave, knit, or braid, or to adjust the porosity of the wearable article.

In additional to the embodiments disclosed herein, properties of the smart fiber can be used to change the friction characteristics on the surface of a wearable article. Applying an external force to the smart material can change it between a slippery state and a non-slippery state. For example the sole on a shoe can be changed between a slippery state and a nonslippery state. In another example, the inner surface of a wearable article such as a prosthetic device or safety equipment can be changed to a slippery state to make it easier to put wearable article onto a person's body and then a non-slippery state to help hold the wearable article in place.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:
1. A haptic zipper, comprising:
a first chain including teeth;
a second chain, opposing the first chain, including teeth;
a slider, coupled to the first chain and the second chain, to mesh or disengage opposing teeth of the first chain and the second chain;
an actuator coupled to the slider;
an antenna to receive an input signal from a remote device over a wireless connection, the input signal including data related to a haptic effect; and
a controller, coupled to the actuator and the antenna, configured to process the input signal, generate a haptic drive signal based on the data, and transmit the haptic drive signal to the actuator to render the haptic effect.

2. The haptic zipper according to claim 1, wherein the actuator further comprises:
a motor including a drive shaft;
a first gear, coupled to the drive shaft, to engage the teeth of the first chain; and
a second gear, coupled to the drive shaft, to engage the teeth of the second chain.

3. The haptic zipper according to claim 2, wherein when the haptic drive signal causes the motor to rotate the first gear and the second gear in a first direction, the slider moves in the first direction and meshes opposing teeth of the first chain and the second chain.

4. The haptic zipper according to claim 3, wherein when the haptic drive signal causes the motor to rotate the first gear and the second gear in a second direction opposite to the first direction, the slider moves in the second direction and disengages opposing teeth of the first chain and the second chain.

5. The haptic zipper according to claim 4, wherein the haptic drive signal causes the slider to move less than a maximum length of travel in the first direction or the second direction.

6. The haptic zipper according to claim 1, wherein the haptic drive signal causes the slider to move in a pattern or sequence.

7. The haptic zipper according to claim 6, wherein the pattern or sequence includes a plurality of movement intervals.

8. The haptic zipper according to claim 6, wherein the pattern is a velocity pattern or an acceleration pattern.

9. The haptic zipper according to claim 2, further comprising:
a pull-tab coupled to the slider,
wherein the controller is further configured to generate a force feedback signal and transmit the force feedback signal to the actuator, the force feedback signal causing movement of the slider.

10. The haptic zipper according to claim 9, wherein the force feedback signal includes a sequence of virtual detents.

11. The haptic zipper according to claim 10, wherein the sequence of virtual detents includes a plurality of virtual detents that are applied periodically at a distance of slider movement.

12. The haptic zipper according to claim 9, further comprising:
a sensor, coupled to the controller, to measure a position of the slider relative to a stop and transmit slider position data to the controller,
wherein the controller is further configured to generate the force feedback signal when the position of the slider is near the stop.

13. The haptic zipper according to claim 12, wherein the sensor is a force sensor, a proximity sensor, an encoder, or a stepper motor.

* * * * *